(12) United States Patent
Hua et al.

(10) Patent No.: US 12,345,647 B2
(45) Date of Patent: Jul. 1, 2025

(54) PROBE FOR DETECTING TRACE URANYL IONS AND PORTABLE ECL DETECTOR BASED ON THE SAME

(71) Applicant: SOOCHOW UNIVERSITY, Suzhou (CN)

(72) Inventors: Daoben Hua, Suzhou (CN); Ziyu Wang, Suzhou (CN); Jianbin Pan, Suzhou (CN); Jingjuan Xu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 1212 days.

(21) Appl. No.: 17/258,926

(22) PCT Filed: Nov. 20, 2019

(86) PCT No.: PCT/CN2019/119691
§ 371 (c)(1),
(2) Date: Jan. 8, 2021

(87) PCT Pub. No.: WO2021/072900
PCT Pub. Date: Apr. 22, 2021

(65) Prior Publication Data
US 2022/0018783 A1    Jan. 20, 2022

(30) Foreign Application Priority Data
Oct. 17, 2019 (CN) .......................... 201910988730.X (51) Int. Cl.
*G01N 21/66* (2006.01)
*C08G 61/12* (2006.01)
(Continued)

(52) U.S. Cl.
CPC .......... *G01N 21/66* (2013.01); *C08G 61/122* (2013.01); *G01N 33/1813* (2013.01);
(Continued)

(58) Field of Classification Search
CPC ...................................................... G01N 21/66
(Continued)

(56) References Cited

FOREIGN PATENT DOCUMENTS

| CN | 108821998 A | 11/2018 |
|---|---|---|
| CN | 109946279 A | 6/2019 |

(Continued)

OTHER PUBLICATIONS

Gao, "Tetraphenylethene modified-ketoiminate boron complexes bearing aggregation-induced emission and mechanofluorochromism" Jan. 2017, Royal Society of Chemistry RSC adv., 2017, 7, 1348-1356 (Year: 2017).*

(Continued)

*Primary Examiner* — Paul S Hyun
*Assistant Examiner* — Emily R. Berkeley
(74) *Attorney, Agent, or Firm* — SZDC Law PC (57) ABSTRACT

A high-sensitivity, high-selectivity and portable detection method for trace uranyl ion is described. The method has an ultralow detection limit of 11 pM/2.6 ppt and is useful in precise monitoring of the uranium content in agricultural and sideline products, foods, environments and so on. The test instrument is miniaturized and low in cost to achieve high-precision portable measurement in the field. A conjugated polymer with aggregation-induced emission (AIE) activity is synthesized, and prepared into Pdots, and a uranyl-responsive electrochemiluminescence (ECL) probe is developed by modifying the Pdots with DNA or RNA, which serves as an adsorption ligand of uranyl ion. The probe exhibits good biocompatibility. The ECL technology can be used in uranyl ion detection and the method has extremely high sensitivity. A uranyl ion probe with AIE activity is also disclosed, which can be applied in portable precise monitoring of trace uranyl ion by means of the ECL technology.

10 Claims, 6 Drawing Sheets

(51) Int. Cl.
  *G01N 33/18* (2006.01)
  *B82Y 20/00* (2011.01)
  *B82Y 40/00* (2011.01)

(52) U.S. Cl.
  CPC ............... *B82Y 20/00* (2013.01); *B82Y 40/00* (2013.01); *C08G 2261/143* (2013.01); *C08G 2261/148* (2013.01); *C08G 2261/18* (2013.01); *C08G 2261/323* (2013.01); *C08G 2261/411* (2013.01); *C08G 2261/522* (2013.01); *C08G 2261/94* (2013.01)

(58) Field of Classification Search
  USPC ......................................................... 436/172
  See application file for complete search history.

(56) References Cited

FOREIGN PATENT DOCUMENTS

| CN | 20190106022 A | 9/2019 |
| CN | 110294837 A | 10/2019 |
| WO | 2017184914 A1 | 10/2017 |

OTHER PUBLICATIONS

Gao (Year: 2017).*
Dai et al. "A study on tunable AIE (AIEE) of boron ketoiminate-based conjugated polymers for live cell imaging" Polym. Chem., 2015, 6, 5070 (Year: 2015).*
Wang et al., "Improved AIE-Active Probe with High Sensitivity for Accurate Uranyl Ion Monitoring in the Wild Using Portable Electrochemiluminescence System for Environmental Applications" Adv. Funct. Mater. 2020, 30, 2000220 (Jun. 2, 2020).
Ziolkowski et al., "Electrochemical uranyl biosensor with DNA oligonucleotides as receptor layer" Anal Bioanal Chem (2012) 402:2259-2266 (Dec. 1, 2013).
Xu et al. "Conjugated microporous polymers bearing phosphonate ligands as an efficient sorbent for potential uranium extraction from high-level liquid wastes" Journal of Materials Chemistry A, No. 6, 13894-13900 (Jun. 21, 2018).
Wang, "The desin, synthesis and applications of multi-component AIE-active functional conjugated polymers" Ph.D. dissertation, Nanjing University (Apr. 15, 2019).
Yuan, "The study on the novel methods for the rapid and on-site detection of uranyl ion" Master dissertation, Fuzhou University (May 15, 2018).

* cited by examiner

PROBE FOR DETECTING TRACE URANYL IONS AND PORTABLE ECL DETECTOR BASED ON THE SAME

This application is the National Stage Application of PCT/CN2019/119691, filed on Nov. 20, 2019, which claims priority to Chinese Patent Application No. 201910988730.X, filed Oct. 17, 2019, which is incorporated by reference for all purposes as if fully set forth herein.

FIELD OF THE INVENTION

The present invention relates to the field of uranyl ion detection, and more particularly to a probe for accurately monitoring trace uranyl ions in agricultural and sideline products, food, environments and so on, as well as a portable ECL detector based on the probe.

DESCRIPTION OF THE RELATED ART

As the increasingly wide use of nuclear technology, the actinide element uranium (U) and its compounds have become a series of important industrial materials widely used in various fields such as civil nuclear fuel, military nuclear industry. The toxicity of uranium compounds is mainly manifested as radiological toxicity and heavy metal toxicity, which can harm the bones, circulatory system and urinary system as well as inducing lung cancer. Therefore, the pollution by uranium compounds due to nuclear leakage and uranium milling tailings will cause serious social and environmental problems, which has become an important issue in the fields of environmental science and energy science. Since uranyl ion is mainly present form of uranium element (including $UO_2(NO_3)_2$, $UO_2(OH)^-$ and $UO_2(CO_3)_3^{4-}$) in the environment, developing uranyl ion probes with high sensitivity and selectivity to realize simple and accurate monitoring of trace uranyl has attracted wide attention in agricultural and sideline products, food, environments.

At present, the widely applied methods for detecting uranyl ions mainly include fluorescent probes, absorption spectrometry, colorimetry, electrochemical detection, and ICP-MS, etc.

In fluorescent probes, quantum dots (QDs), organic small molecular fluorescence probes, conjugated organic polymers and other fluorescence molecules have been widely reported to detect the concentration of uranyl ion. Although QDs often give high fluorescence quantum yields, they contain heavy metal elements such as Cd, which can exhibit obvious biological toxicity and pose certain potential threats to the environment. At present, most of the existing small molecular organic fluorescence probes and conjugated polymer fluorescent probes often suffer from aggregation-caused quenching (ACQ) performance. This property can greatly reduce fluorescence quantum yield in an aqueous solution, causing an adverse effect on uranyl ion detection in natural environment. Absorption spectroscopy can detect uranyl ions by measuring absorption spectra before and after coordination with certain ligands. Colorimetry can visibly detect the uranyl ions by observing the color changes of corresponding ligands before and after coordination with the uranyl ions. Although colorimetry is intuitive, it is difficult and vulnerable to environmental interference, and suffers from poor selectivity. The electrochemical detection detects the uranyl ions by measuring cyclic voltammetry data in the redox waveform before and after coordination of the uranyl ions with a ligand.

The existing uranyl ion detection methods have relatively high detection limit and low sensitivity. The detection limit is close to or higher than the uranyl ion concentration in normal environment, and it is impossible to accurately monitor the uranyl ion in the environment in real time. Although ICP-MS has high accuracy, the device is expensive and bulky, which is impossible for using it in the wild. Therefore, improving the detection sensitivity and miniaturization of the device are also problems to be solved urgently.

SUMMARY OF THE INVENTION

In order to solve the defects of low biocompatibility, large environmental impact, high detection limit, and low photon yield in aqueous solutions in the existing detection methods, an object of the present invention is to provide a probe for detecting trace uranyl ions as well as an ECL detector based on the probe. Compared with ICP-MS, the ECL device gives lower cost and smaller size, and can even be further miniaturized, which can solve the problems of ICP-MS method. The present invention provides a uranyl ion probe with AIE activity, which realizes high sensitivity, high selectivity and portable detection of trace uranyl ion in the environment using ECL technology.

The first object of the present invention is to provide a probe for detecting trace uranyl ions, which comprises AIE-active conjugated polymer dots (Pdots) and a nucleotide sequence modified on the surface of Pdots. The nucleotide sequence is a DNA and/or RNA sequence, and the conjugated polymer in the Pdots has the structural Formula (1):

(1)

where $R^1$ is an alkyl group, alkoxy group, substituted alkyl group or substituted alkoxy group containing 1-20 carbon atoms, in which the substituents in the substituted alkyl group and the substituted alkoxy group are independently selected from the group consisting of amino, carboxyl, hydroxyl, an ether bond, halo, a phosphoric acid group, an aldehyde group, a sulfonic acid group, a thioether bond, an ester group, amido, a Schiff base, an oximido, aryl, a sulfone group and a sulfoxide group; and n=2-300.

Preferably, $R^1$ is an alkyl group containing 1-20 carbon atoms; more preferably, R is n-octyl.

Preferably, the particle size of the Pdots is 10 nm-100 nm.

Preferably, the length of the nucleotide sequence is 5-100 bp.

Preferably, the nucleotide sequence is a DNA sequence.

A second object of the present invention also provides a method for preparing the probe for detecting trace uranyl ions, which includes the following steps:
(1) subjecting a first ATE-active monomer of Formula (2) and a second ATE-active monomer of Formula (3) to Suzuki coupling polymerization reaction to obtain a conjugated polymer of Formula (1), in which Formulas (2) and (3) are shown below:

where $R^1$ is an alkyl group, alkoxy group, substituted alkyl group or substituted alkoxy group containing 1-20 carbon atoms, in which the substituents in the substituted alkyl group and the substituted alkoxy group are independently selected from the group consisting of amino, carboxyl, hydroxyl, an ether bond, halo, a phosphoric acid group, an aldehyde group, a sulfonic acid group, a thioether bond, an ester group, amido, a Schiff base, an oximido, aryl, a sulfone group and a sulfoxide group;
$R^2$ is a pinacol borate ester group, a trialkyltin group, a boric acid group, halo, ethynyl or vinyl; and
$R^3$ is halo, a pinacol borate ester group, a trialkyltin group, a boric acid group, ethynyl or vinyl;
(2) injecting a solution of the conjugated polymer in an alcohol into water, and removing the alcohol solvent, to obtain an aqueous solution of Pdots; and
(3) mixing the aqueous solution of the Pdots with polyethylene glycol and a buffer; then adding a nucleotide sequence modified with an amino group at the 5' end and a cross-linking agent, where the nucleotide sequence is a DNA sequence and/or RNA sequence; and mixing well and reacting to obtain the probe for detecting trace uranyl ions.

Preferably, in Step (1), $R^1$ is n-octyl, $R^2$ is a pinacol borate ester group, and $R^3$ is halogen.

Preferably, in Step (2), the concentration of the solution of the conjugated polymer in an alcohol is 0.01-1.00 mg/mL.

Preferably, in Step (2), the concentration of the aqueous solution of Pdots is 0.01-1.00 mg/mL.

Preferably, in Step (2), the particle size of the Pdots is 10 nm-100 nm.

Preferably, in Step (3), the molecular weight of polyethylene glycol is 100-100000.

Preferably, in Step (3), the buffer is HEPES (4-hydroxyethylpiperazine ethanesulfonic acid) buffer.

Preferably, in Step (3), the crosslinking agent is EDC (1-(3-dimethylamino-propyl)-3-ethylcarbodiimide hydrochloride).

Preferably, in Step (3), the nucleotide sequence is a DNA sequence. Preferably, from the 3' end to the 5' end, the nucleotide sequence of the DNA is: taa ttc tgt gta tgt gtc tgt.

A third object of the present invention is to provide a portable ECL detector for detecting trace uranyl ions. The ECL detector detects trace uranyl ions in the presence of an amine co-reactant reagent and includes a working electrode modified with the probe for detecting trace uranyl ions.

Preferably, the working electrode is a GCE electrode or a gold electrode.

Preferably, the ECL detector includes an electric signal applying unit, a luminescence cell, a photomultiplier tube, and a signal amplifying and processing unit. A positive and a negative electrode of the electric signal applying unit are respectively connected to the working electrode and a counter electrode. The luminescence cell is used for accommodating the test solution and the amine co-reactant reagent, the working electrode and the counter electrode are positioned in the luminescence cell. The photomultiplier tube is arranged facing directly the luminescence cell, and the photomultiplier tube is electrically connected to the signal amplification and processing unit.

Preferably, the detection limit of uranyl ions is 11 pM/2.6 ppt.

In a preferred embodiment, the concentration of the amine co-reactant reagent is 25 mM. Preferably, the amine co-reactant reagent is a tertiary amine. More preferably, the amine co-reactant reagent is tri-n-propylamine (TPrA).

Preferably, the electric signal applying unit is a constant-voltage DC power supply.

Preferably, the voltage applied by the electric signal applying unit is 0.50V-2.00V.

The uranyl ion probe and the portable ECL detector based on the uranyl ion probe according to the present invention can be used for accurate monitoring of trace uranyl ions in agricultural and sideline products, foods, environments and so on.

A fourth object of the present invention is to provide a method for detecting trace uranyl ions, using the above-mentioned ECL detector for detecting trace uranyl ions, which includes the following steps:
(1) detecting the ECL signal intensity values of uranyl ion standard solutions by the ECL detector, and establishing a correlation diagram between the uranyl ion concentrations and the ECL signal intensities according to the detection results; and
(2) detecting the ECL signal intensity $A_x$ of a test solution by the ECL detector, where the content of uranyl ions in the test solution is unknown, and determining the uranyl ion concentration in the test solution according to the corresponding relationship of the ECL signal intensity $A_x$ in the correlation diagram.

By means of the above technical solutions, the present invention has the following advantages.

The probe for detecting trace uranyl ions of the present invention includes conjugated polymer dots (Pdots) and a nucleotide modified thereon, where the Pdots are prepared by a novel aggregation-induced emission (AIE)-active conjugated polymer, and the phosphate group in the nucleotide functions as an adsorption ligand of uranyl ions. In this way, a new uranyl-responsive electrochemiluminescence (ECL) probe is developed. This probe overcomes the defect of luminescence quenching of the traditional uranyl luminescence probe in an aqueous solution by making use of the AIE characteristic of Pdots. The conjugated polymer does not contain heavy metal ions, and gives better biocompatibility. The ECL probe of the present invention also has extremely high uranyl ion selectivity.

The ECL technology has the advantages of no interference by background signal, simple operation and good reproducibility, which greatly improves the sensitivity of uranyl ion detection. Therefore, the present invention achieves the highly sensitive detection of trace uranyl ions with a detection limit of 11 pM/2.6 ppt, which is at least two orders of magnitude lower than the known organic small molecular luminescence probes and conjugated polymers. This probe achieves the accurate detection of trace uranyl ions in sea water and lake water. The portable ECL detector based on the probe of the present invention realizes rapid and accurate trace detection of uranyl ions in the field.

The above description is only a summary of the technical solutions of the present invention. To make the technical means of the present invention clearer and implementable in accordance with the disclosure of the specification, the preferred embodiments of the present invention will be described in detail with reference to the accompanying drawings.

LIST OF REFERENCE NUMERALS

1: working electrode, 2: counter electrode, 3: constant voltage DC power supply, 4: wire, 5: luminescence cell, 6: photomultiplier tube, 7: electrical signal applying unit, 8: signal amplification and processing unit.

DETAILED DESCRIPTION OF THE PREFERRED EMBODIMENTS

The specific embodiments of the present invention will be described in further detail with reference to the accompanying drawings and specific embodiments. The following embodiments are intended to illustrate the present invention, instead of limiting the scope of the present invention.

Example 1

Figure 1:
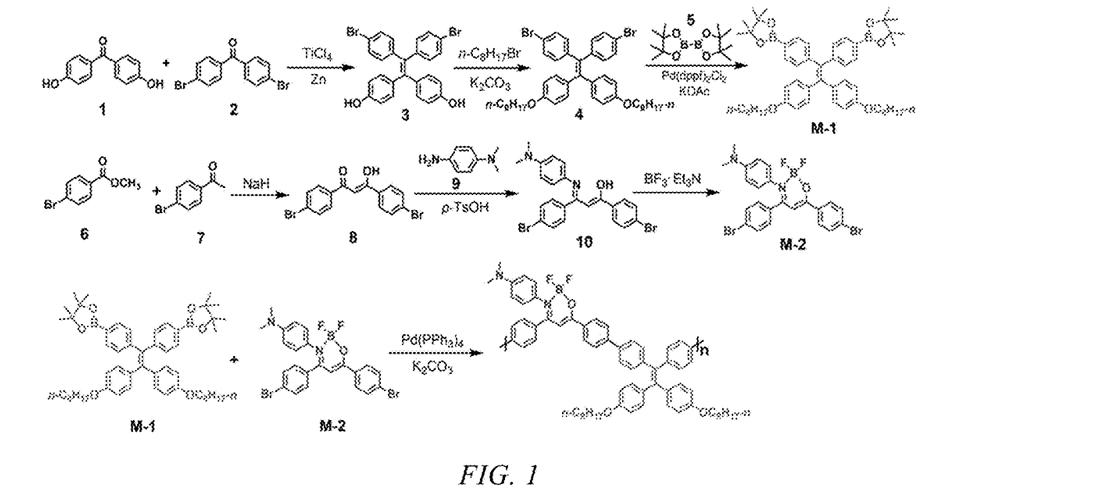
FIG. 1 is a schematic diagram showing the synthesis route of a conjugated polymer with AIE activity of the present invention.

This example provides a method for preparing an ATE-active conjugated polymer. The synthesis route was shown in FIG. 1. The specific steps were carried out as follows:

The synthesis of Compound 4 was as described in *ACS Appl. Mater. Interfaces* 2017, 9, 11546-11556. The synthesis of Monomer M-2 was as described in *Polym. Chem.* 2015, 6, 5070-5076.

Synthesis of Monomer M-1: Compound 4 (2.28 g, 3 mmol), Compound 5 (3.08 g, 12 mmol), potassium acetate (2.40 g, 12 mmol), and Pd(dppf)$_2$Cl$_2$ (0.3 g, 5% mmol) were dissolved in DMF (60 mL) and, heated to 120° C. under Ar atmosphere for 24 h. The reaction solution was poured into water (200 mL), and extracted with ethyl acetate. The organic phase was washed twice with water, and purified by column chromatography on silica gel (mobile phase, ethyl acetate:petroleum ether=1:30) to obtain the product (1.61 g, yield 64.0%). The NMR test results are shown below:

$^1$H NMR (400 MHz, CDCl$_3$) δ7.52 (d, J=8.1 Hz, 4H), 7.00 (d, J=8.1 Hz, 4H), 6.90 (d, J=8.7 Hz, 4H), 6.60 (d, J=8.8 Hz, 4H), 3.86 (t, J=6.6 Hz, 4H), 1.81-1.66 (m, 4H), 1.50-1.37 (m, 5H), 1.37-1.24 (m, 40H), 0.88 (t, J=6.8 Hz, 6H). $^{13}$C NMR (100 MHz, CDCl$_3$) δ157.80, 147.35, 141.33, 138.76, 135.96, 134.10, 132.61, 130.84, 113.55, 83.66, 67.78, 31.82, 29.40, 29.33, 29.24, 26.09, 24.90, 22.67, 14.11.

Synthesis of conjugated polymer: M-1 (0.16 g, 0.19 mmol), M-2 (0.10 g, 0.19 mmol), Pd(PPh$_3$)$_4$ (0.04 g, 5% e.q.), and K$_2$CO$_3$ (1.3 g) were dissolved in toluene (15 mL), ethanol (8 mL) and water (4 mL). The mixture was further refluxed for 3 d. The organic phase was dried over Na$_2$SO$_4$. After the solvent being removed by a rotary dryer, the mixture was dissolved in a small amount of THF to be dropped into n-hexane (100 mL). The solvent was filtered to obtain the conjugated polymer (0.10 g, yield 53.8%). The $^1$H NMR and GPC test results are shown below:

$^1$H NMR (400 MHz, CDCl$_3$) δ 8.06-7.99 (m, 3H), 7.73-7.63 (m, 5H), 7.50-7.38 (m, 8H), 7.12-7.11 (m, 2H), 6.98-6.97 (m, 2H), 6.77-6.76 (m, 3H), 6.66-6.64 (m, 3H), 6.53-6.51 (m, 3H), 3.89-3.86 (m, 4H), 2.88 (s, 6H), 1.77-1.72 (m, 6H), 1.42-1.41 (m, 3H), 1.29-1.24 (m, 15H), 0.87-0.86 (m, 6H). GPC data: $M_w$=19060, $M_n$=16720, PDI=1.14.

Figure 2:
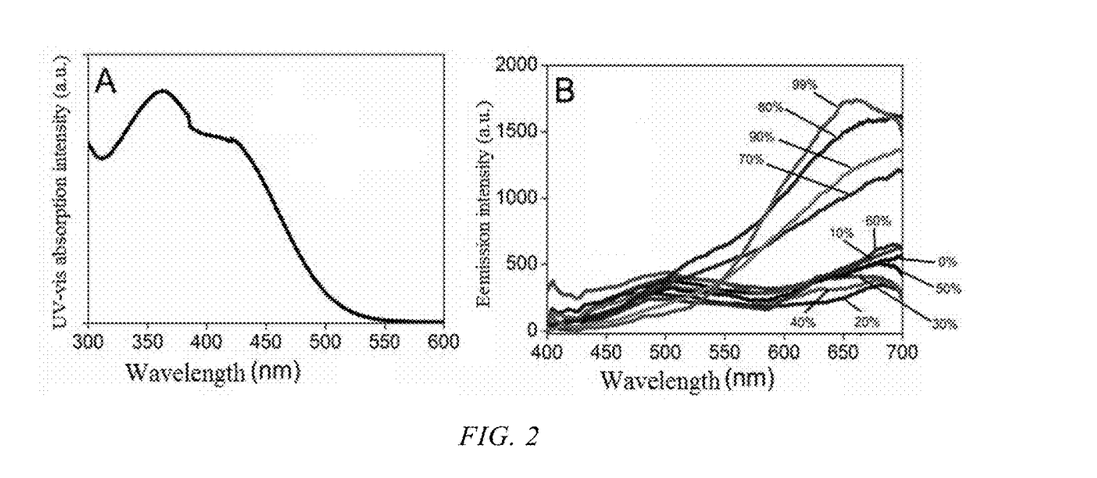
FIG. 2 shows the test results by UV absorption spectrometry and fluorescence spectrometry of a THF solution of a conjugated polymer.
Figure 3:
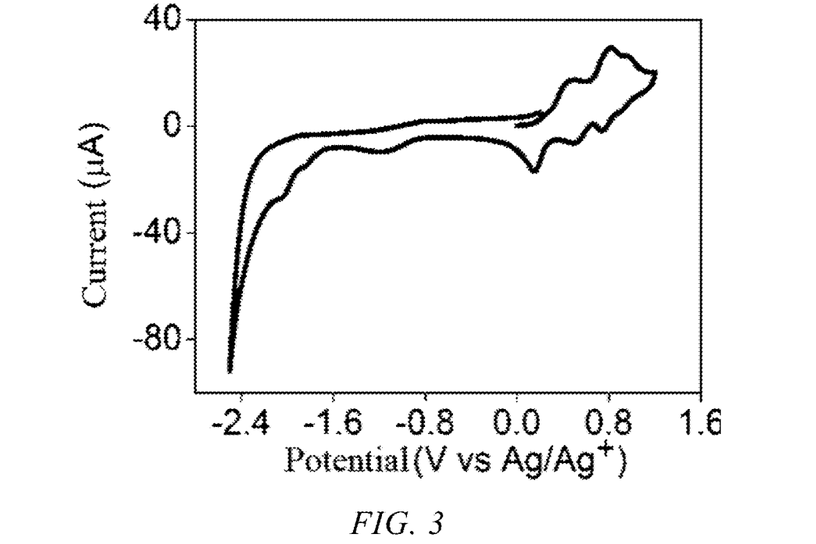
FIG. 3 is a cyclic voltammogram of a conjugated polymer.

The photoelectric performance test results of the conjugated polymer prepared above are shown in FIG. 2. FIGS. 2A and 2B are the UV absorption spectrum of the conjugated polymer and the fluorescence spectra in THF-water mixtures with different water fractions. In FIG. 2B, the excitation wavelength is 370 nm, and the concentration of conjugated polymer in each solution is 1×10$^{-5}$ mol/L. As shown in FIG. 2A, the conjugated polymer exhibits an absorption peak of the conjugated backbone at 363 nm, and a shoulder peak at 421 nm, which could be attributed to the intramolecular charge transfer (ICT) caused by the electron donor-acceptor (D-A) structure. As shown in FIG. 2B, the conjugated polymer shows obvious AIE behavior in the deep-red/near-infrared region under an excitation wavelength of 370 nm. FIG. 3 shows a cyclic voltammogram (CV) data of the conjugated polymer in 0.1 M Bu$_4$NBF$_4$ CH$_2$Cl$_2$ solution tested by an GCE electrode, in which the two oxidation peaks at +0.487 V and +0.815 V can be attributed to the oxidation peaks of the TPE moiety. The reduction peak appears at −1.711 V, and the LUMO, HOMO, and band gap values can be calculated as −2.849 eV, −4.824 eV and 1.975 eV, respectively. The optical band gap from the emission spectrum was calculated as 1.890 eV ($E_g=1239.8/\lambda$ (eV)).

Example 2

The present invention provides a method for preparing the probe for detecting trace uranyl ions, which includes the following steps:

The conjugated polymer prepared in Example 1 was dissolved in ethanol with a concentration of 0.15 mg/mL. Then the conjugated polymer solution (1 mL) was poured into water (10 mL), and the ethanol was removed by vacuum distillation to obtain an aqueous Pdots solution (10 mL).

A PEG aqueous solution (5% w/v), and HEPES buffer (1 M) were added to the aqueous Pdots solution (0.15 mg/mL), and then $NH_2$-DNA (1 μM) and EDC (5 mg/mL) were added to the mixture and shaken for 0.5 h to obtain DNA-Pdots. The DNA sequence is: 3'-taa ttc tgt gta tgt gtc tgt-5'-$NH_2$.

In this example, the base sequences in the DNA sequence can be selected randomly, and the DNA sequence can also be replaced by an RNA sequence.

Figure 4:
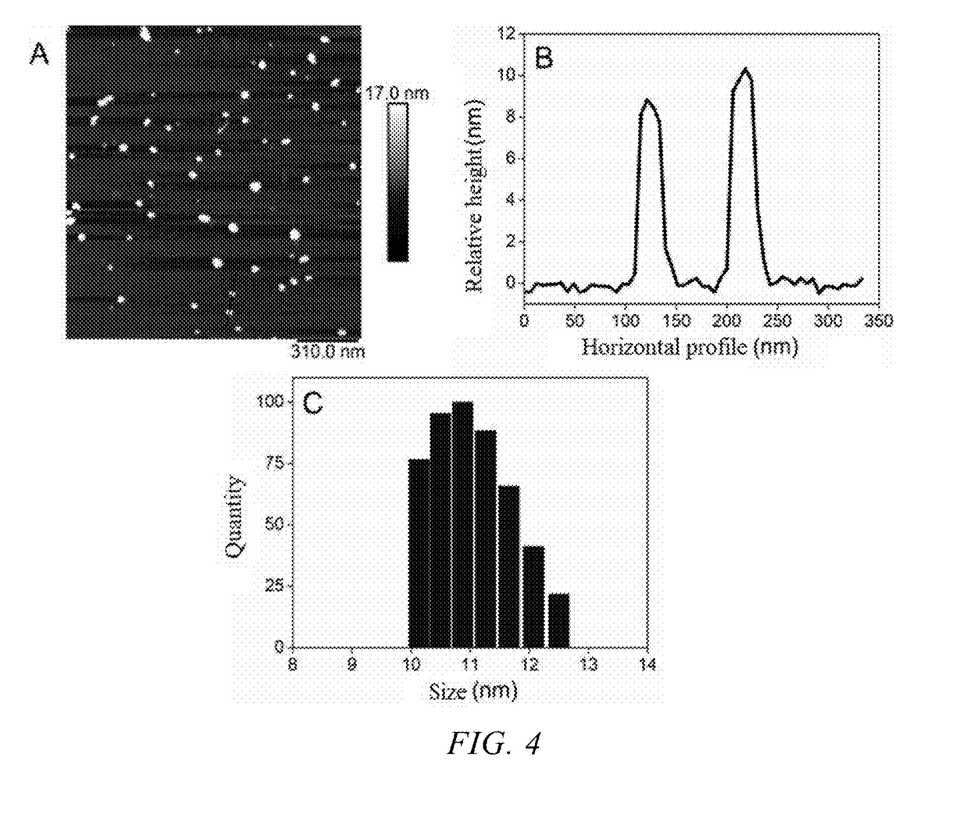
FIG. 4 shows the test results by AFM and DLS of Pdots.

FIG. 4(A) is an AFM image of Pdots; FIG. 4(B) shows the relative height of the black line in the AFM image; and FIG. 4(C) shows the DLS test result of Pdots. Both AFM image and DLS data show that the average particle size of Pdots is about 10 nm.

Figure 5:
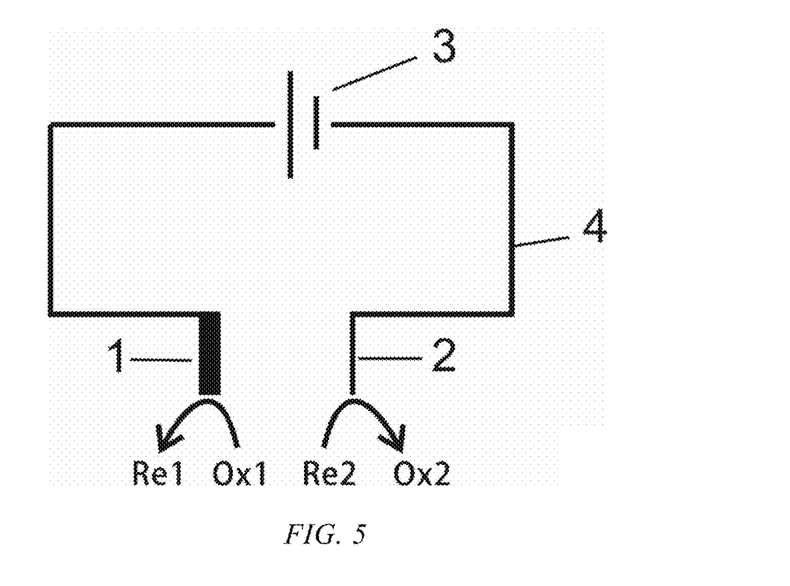
FIG. 5 is a schematic diagram an ECL device.

Pdots were modified on a working electrode and assembled into a simple ECL device. As shown in FIG. 5, the modified working electrode was inserted into the luminescence cell, and 25 mM tri-n-propylamine (TPrA) buffer or 0.1 M PBS buffer (pH=7.4) was injected. A counter electrode and a reference electrode were inserted, and then the DNA-Pdots modified electrode was used as the working electrode. Test conditions: sweep speed: 100 mV/s, PMT: 600 V, $\lambda_{ex}$=370 nm. When the potential was swept to +0.880 V, an optical signal was emitted, and when the potential was swept to +1.264 V, the optical signal was the strongest.

Figure 6:
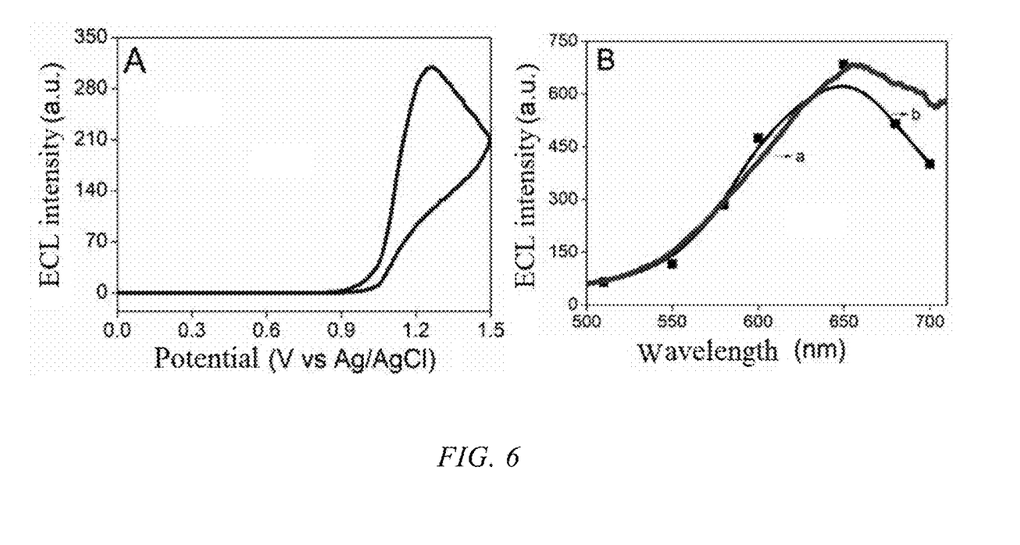
FIG. 6 shows the ECL signal test results and ECL spectrum of Pdots.

As shown in FIG. 6A, Pdots cannot give obvious ECL signal in annihilation state. The obvious anodic ECL signal can be observed only when TPrA is added as a co-reactant reagent. The peak value of the ECL signal is +1.264V and the onset potential is +0.880V. The ECL mechanism is as follows:

(1)

(2)

(3)

(4)

(5)

As shown in FIG. 6B, the ECL spectrum of Pdots is basically overlapped with its fluorescence spectrum, which indicates that the ECL mechanism follows the band gap emission model.

Figure 7:
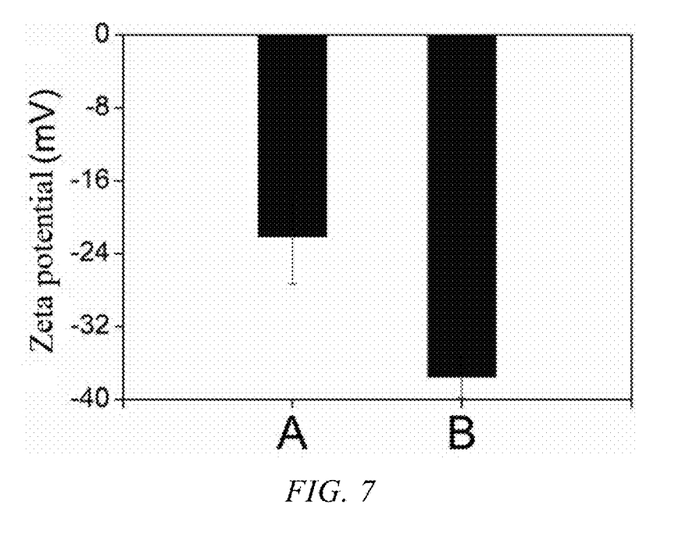
FIG. 7 shows the zeta potential of Pdots before (A) and after (B) modification with the single-strand DNA.

Single-stranded DNA is modified on Pdots for using the phosphate group on the DNA strand as a ligand for binding uranyl ions. The ECL signal of Pdots can be enhanced through the resonance energy transfer (RET) process from uranyl ions to Pdots, thereby realizing the high sensitive and selective detection of uranyl ions. FIG. 7 shows the zeta potential of Pdots before (A) and after (B) modification with single-stranded DNA. The zeta potential of Pdots is −22.1 mV before modification with DNA. After modification with DNA, the potential rises to −37.5 mV, indicating the successful modification of Pdots.

Figure 8:
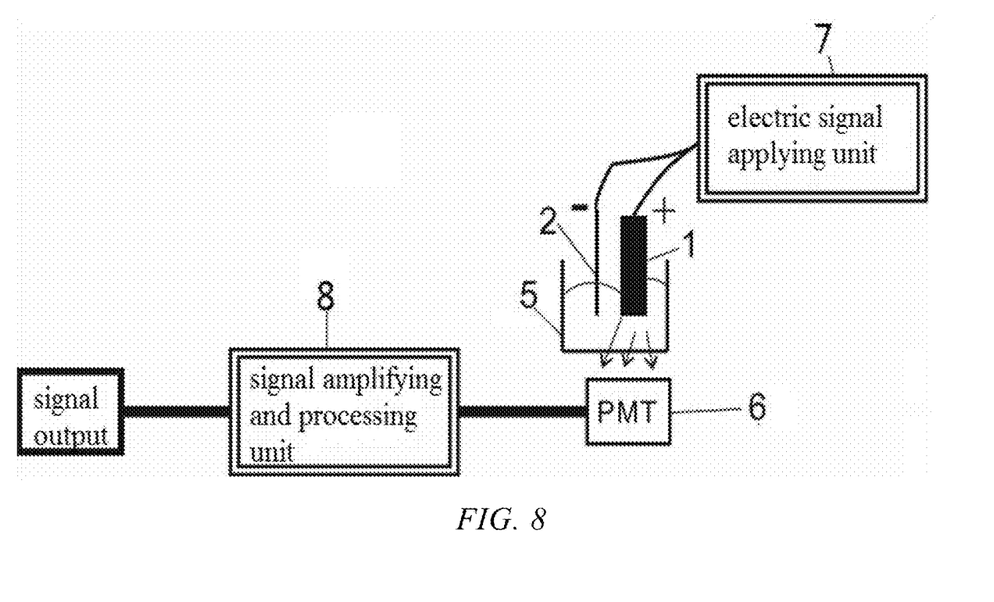
FIG. 8 is a schematic diagram of an ECL detector.

As shown in FIG. 8, this example also provides an ECL detector for detecting trace uranyl ions. The ECL detector comprises an electrical signal applying unit, a luminescence cell, a photomultiplier tube, and a signal amplifying and processing unit. A positive and a negative electrode of the electric signal applying unit are respectively connected to the working electrode and the counter electrode, where the working electrode is modified with the above-mentioned probe for detecting trace uranyl ions. The luminescence cell is used for accommodating a test solution and an amine co-reactant reagent, the working electrode and the counter electrode are positioned in the luminescence cell, the photomultiplier tube is arranged facing directly the luminescence cell, and the photomultiplier tube is electrically connected to the signal amplification and processing unit.

The working electrode is modified as follows:

GCE electrodes were polished with $Al_2O_3$ powder. The DNA-Pdots obtained in Example 2 were mixed with uranyl solutions (different concentrations), natural water samples or interfering ion solutions. The GCE electrodes were immersed in the above mixed solution to allow the DNA-Pdots to be modified on the GCE electrode.

Figure 9:
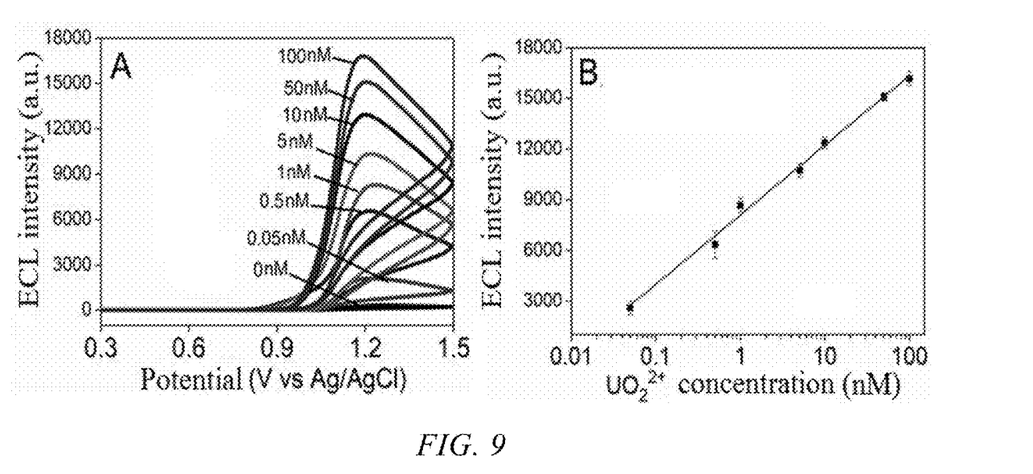
FIG. 9 shows the ECL signal of Pdots in the presence of different concentrations of uranyl ($UO_2^{2+}$) and a calibration curve of the ECL intensity against the logarithmic concentration of uranyl.

FIG. 9 shows the ECL signals of Pdots in the presence of different concentrations of $UO_2^{2+}$ (A), and the calibration curve of the ECL intensity against the logarithmic concentration of uranyl ion (B). Sweep speed: 100 mV/s, PMT: 600 V. As shown in FIG. 9A, as the uranyl ion concentration increases from 0.05 nM to 100 nM, the ECL signal intensity of Pdots gradually increased. The ECL signal intensity I is obviously linear with the logarithmic concentration C of uranyl in this region (FIG. 9B, I=8109.7+4108.31 gC, $R^2$=0.996). The detection limit could be calculated as 11 pM/2.6 ppt, which is at least two orders of magnitude lower than that of the currently known uranyl ion luminescent probe, especially the known AIE-active probe.

Figure 10:
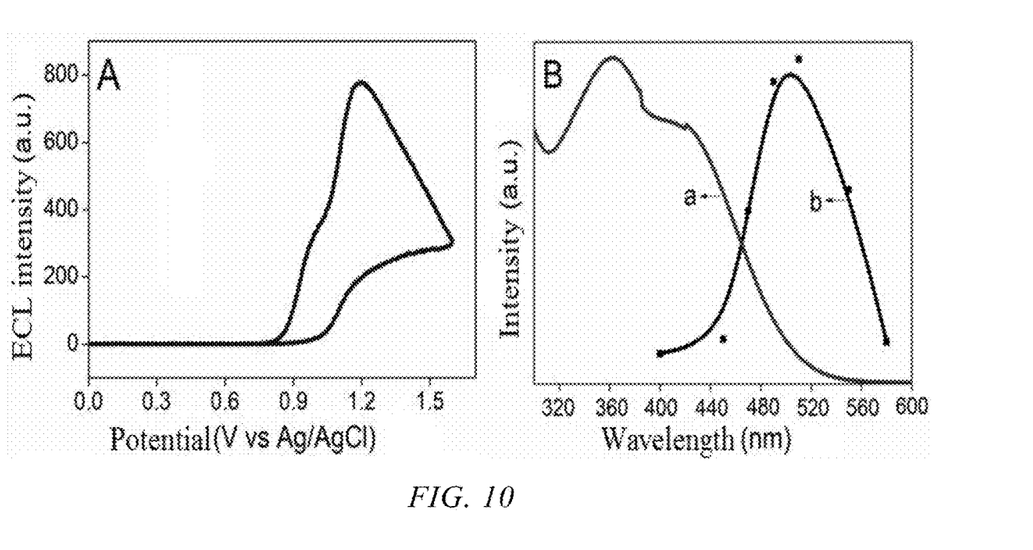
FIG. 10 demonstrates the RET process from uranyl to Pdots.

In order to confirm the RET process from uranyl ions to Pdots, FIG. 10A shows the ECL signal of uranyl ion in 0.1 M PBS (pH 7.4) containing 25 mM TPrA, and FIG. 10(B) shows the UV-vis spectrum (a) of the conjugated polymer solution in THF and the ECL spectrum (b) of uranyl ions in 0.1 M PBS (pH 7.4) containing 25 mM TPrA. Sweep speed: 100 mV/s, PMT: 600 V. As shown in FIG. 10A, with 25 mM TPrA as a co-reactant regent, the uranyl ion shows a significant ECL signal in the anodic region, with an emission peak at +1.120 V with the onset potential as +0.791 V. The ECL spectrum of $UO_2^{2+}$ ion gives an emission peak around 500 nm, which overlaps with the UV-vis absorption spectrum of the conjugated polymer in the region of 400 to 560 nm. This phenomenon indicated the RET process from uranyl ion to Pdots (FIG. 10B).

Figure 11:
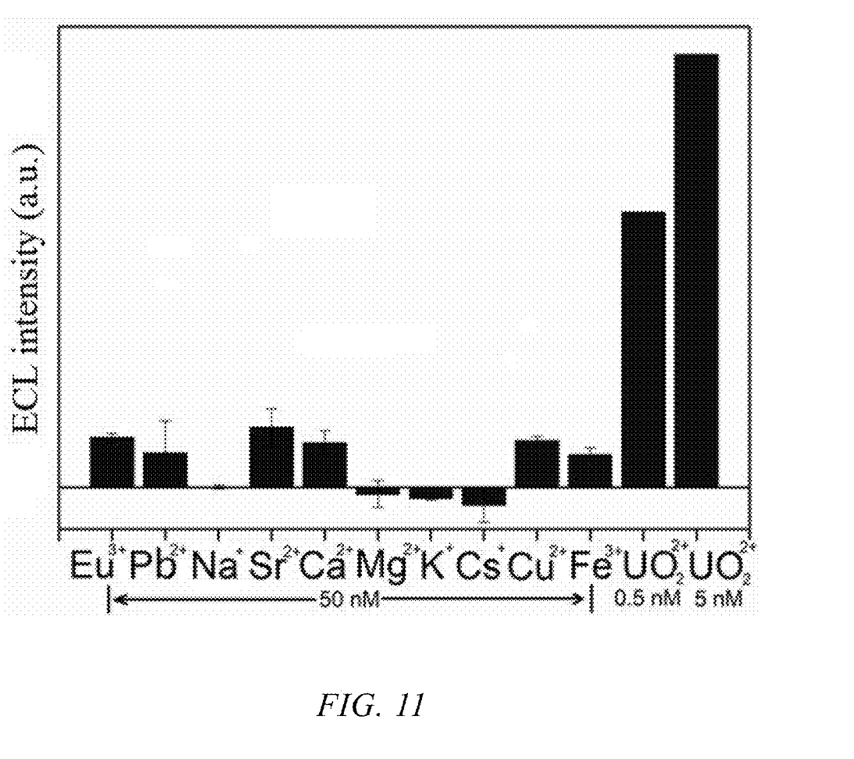
FIG. 11 illustrates the ECL signal intensity of interfering ions and uranyl.

To confirm the selectivity of the probe, several interfering ions were selected for comparison with $UO_2^{2+}$ ions. $K^+$, $Ca^{2+}$, $Na^+$, $Mg^{2+}$ and $Sr^{2+}$ are main cations contained in sea water. $Eu^{3+}$ is an ion with ECL signal, which is closely related to the adsorption and detection of $UO_2^{2+}$ ions. $Cs^+$ often coexists with $UO_2^{2+}$, and $Cu^{2+}$, $Fe^{3+}$ and $Pb^{2+}$ are representative of heavy metals in the environment. Compared with $UO_2^{2+}$ ions with a concentration of 0.5 nM or 5 nM, these interfering ions have almost no significant signal enhancement even in a solution of 50 nM (FIG. 11). The selectivity of this probe can be attributed to i) the specific adsorption of $UO_2^{2+}$ ions by the phosphate groups on the DNA strand; and ii) the non-ECL property of interfering ions in anodic region. The experimental results confirm the excellent selectivity of ECL probe for $UO_2^{2+}$ based on Pdots.

In order to further confirm the applicability of this probe, the concentration of uranyl ions in some practical water samples was determined in this example, including water samples from Bohai Sea (Tianjin, China), Luoma Lake (Xuzhou, China), Dushu Lake (Suzhou, China), and Qiandao Lake (Hangzhou, China) (Table 1). It can be observed that the results obtained by ECL is quite close to ICP-MS, indicating the practical application of this new ECL probe in environment field.

TABLE 1

Comparison of the uranyl concentration values obtained by ECL and ICP-MS

|  | Water source | Test result by ECL (ppb) | Test result by ICP-MS (ppb) | |
|---|---|---|---|---|
|  |  |  | Result (ppb) | RSDs (%) |
| Sea water | Bohai Sea (Tianjin) | 3.24 ± 0.05 | 2.05 | 1.92 |
| Fresh water | Luoma Lake (Xuzhou, Jiangsu Province) | 1.48 ± 0.02 | 1.25 | 0.98 |
|  | Dushu Lake (Suzhou, Jiangsu Province) | 0.38 ± 0.08 | 0.50 | 0.32 |
|  | Qiandao Lake (Hangzhou, Zhejiang Province) | 0.21 ± 0.01 | 0.15 | 0.35 |

While preferred embodiments of the present invention have been described above, the present invention is not limited thereto. It should be appreciated that some improvements and variations can be made by those skilled in the art without departing from the technical principles of the present invention, which are also contemplated to be within the scope of the present invention.

What is claimed is:

1. A probe for detecting trace uranyl ions, comprising conjugated polymer dots with AIE activity and a nucleotide sequence modified on the surface of the conjugated polymer dots, wherein the nucleotide sequence is a DNA and/or RNA sequence, and the conjugated polymer in the conjugated polymer dots has the structural Formula (1):

(1)

where $R^1$ is an alkyl group, alkoxy group, substituted alkyl group or substituted alkoxy group containing 1-20 carbon atoms, in which the substituents in the substituted alkyl group and the substituted alkoxy group are independently selected from the group consisting of amino, carboxyl, hydroxyl, an ether bond, halo, a phosphoric acid group, an aldehyde group, a sulfonic acid group, a thioether bond, an ester group, amido, a Schiff base, an oximido, aryl, a sulfone group and a sulfoxide group; and n=2-300.

2. A method for preparing a probe for detecting trace uranyl ions according to claim 1, comprising steps of:

(1) subjecting a first AIE active monomer of Formula (2) and a second AIE active monomer of Formula (3) to Suzuki coupling polymerization reaction to obtain a conjugated polymer of Formula (1), in which Formulas (2) and (3) are shown below:

(2)

(3)

where $R^1$ is an alkyl group, alkoxy group, substituted alkyl group or substituted alkoxy group containing 1-20 carbon atoms, in which the substituents in the substituted alkyl group and the substituted alkoxy group are independently selected from the group consisting of amino, carboxyl, hydroxyl, an ether bond, halo, a phosphoric acid group, an aldehyde group, a sulfonic acid group, a thioether bond, an ester group, amido, a Schiff base, an oximido, aryl, a sulfone group and a sulfoxide group;

$R^2$ is a pinacol borate ester group, a trialkyltin group, a boric acid group, halo, ethynyl or vinyl; and $R^3$ is halo, a pinacol borate ester group, a trialkyltin group, a boric acid group, ethynyl or vinyl;

(2) injecting a solution of the conjugated polymer in an alcohol solvent into water, and removing the alcohol solvent, to obtain an aqueous solution of conjugated polymer dots; and (3) mixing the aqueous solution of the conjugated polymer dots with polyethylene glycol and a buffer; then adding a nucleotide sequence modified with an amino group at the 5' end and a cross-linking agent, where the nucleotide sequence is a DNA and/or RNA sequence; and mixing well and reacting to obtain the probe for detecting trace uranyl ions.

3. The preparation method according to claim 2, wherein in Step (2), the particle size of the conjugated polymer dots is 10 nm-200 nm.

4. The preparation method according to claim 2, wherein in Step (2), the concentration of the aqueous solution of the conjugated polymer dots is 0.01-1.00 mg/mL.

5. An ECL detector for detecting trace uranyl ions, wherein the ECL detector detects trace uranyl ions in the presence of an amine co-reactant reagent, and the ECL detector comprises a working electrode modified with the probe for detecting trace uranyl ions according to claim 1.

6. The ECL detector according to claim 5, comprising:
an electric signal applying unit;
a luminescence cell for accommodating a test solution and the amine co-reactant reagent,
a photomultiplier tube directly facing the luminescence cell; and
a signal amplifying and processing unit;
wherein a positive and a negative electrode of the electric signal applying unit are respectively connected to the working electrode and a counter electrode which are positioned in the luminescence cell, and the photomultiplier tube is electrically connected to the signal amplification and processing unit.

7. The ECL detector according to claim 5, wherein the detection limit of uranyl ions is 11 pM.

8. The ECL detector according to claim 5, wherein the concentration of the amine co-reactant reagent is 5-100 mM.

9. The ECL detector according to claim 6, wherein the voltage applied by the electric signal applying unit is 0.50 V-2.00V.

10. A method for detecting trace uranyl ions, by using the ECL detector for detecting trace uranyl ions according to claim 5, comprising steps of:
(1) detecting ECL signal intensities of uranyl ion standard solutions by the ECL detector, and establishing a correlation diagram between the uranyl ion concentrations and the ECL signal intensities according to the detection results; and
(2) detecting an ECL signal intensity $A_x$ of a test solution by the ECL detector, where the content of uranyl ions in the test solution is unknown, and determining the uranyl ion concentration in the test solution according to the corresponding relationship of the ECL signal intensity $A_x$ in the correlation diagram.

* * * * *